United States Patent
Oraevsky (10) Patent No.: US 12,295,706 B2
(45) Date of Patent: May 13, 2025

(54) QUANTITATIVE OPTOACOUSTIC TOMOGRAPHY FOR DYNAMIC ANGIOGRAPHY OF PERIPHERAL VASCULATURE

(71) Applicant: Alexander A. Oraevsky, Houston, TX (US)

(72) Inventor: Alexander A. Oraevsky, Houston, TX (US)

( * ) Notice: Subject to any disclaimer, the term of this patent is extended or adjusted under 35 U.S.C. 154(b) by 1188 days.

(21) Appl. No.: 17/074,371

(22) Filed: Oct. 19, 2020

(65) Prior Publication Data

US 2021/0030280 A1  Feb. 4, 2021

Related U.S. Application Data

(63) Continuation-in-part of application No. 13/748,563, filed on Jan. 23, 2013, now abandoned.

(60) Provisional application No. 61/632,389, filed on Jan. 23, 2012.

(51) Int. Cl.
*A61B 5/02* (2006.01)
*A61B 5/00* (2006.01)
*A61B 5/026* (2006.01)
*A61B 5/145* (2006.01)

(52) U.S. Cl.
CPC .......... *A61B 5/02007* (2013.01); *A61B 5/004* (2013.01); *A61B 5/0095* (2013.01); *A61B 5/026* (2013.01); *A61B 5/14542* (2013.01); *A61B 5/14546* (2013.01); *A61B 5/742* (2013.01)

(58) Field of Classification Search
CPC ... A61B 5/02007; A61B 5/0095; A61B 5/004; A61B 5/026; A61B 5/14542; A61B 5/14546; A61B 5/742
See application file for complete search history.

(56) References Cited

U.S. PATENT DOCUMENTS

| | | | |
|---|---|---|---|
| 2008/0173093 A1* | 7/2008 | Wang | A61B 5/0095 73/602 |
| 2011/0306865 A1* | 12/2011 | Thornton | A61B 5/0059 600/407 |
| 2012/0125107 A1* | 5/2012 | Emelianov | G16H 50/30 73/579 |

* cited by examiner

*Primary Examiner* — Chao Sheng
(74) *Attorney, Agent, or Firm* — Benjamin Aaron Adler (57) ABSTRACT

Provided herein are quantitative optoacoustic tomography systems and methods for dynamic of functional parameters in a subject, for example, to assess conditions of the peripheral vasculature. The system generally has a pulsed laser, a fiberoptic optic bundle light delivery system, and imaging module, an array of ultrawide-band ultrasonic transducers, a circulation system, and electronics/computer system for system control and three-dimensional and two-dimensional optoacoustic image visualization. Also provided is a method for quantitative optoacoustic tomography of an appendage where an appendage of a subject is imaged under conditions of normal, maximum and minimum tolerable temperatures and displaying differential anatomical images of peripheral vasculature in the appendage and functional diagnostic parameters as a function of time and temperature. From this data medical conditions of the appendage may be diagnosed.

15 Claims, 7 Drawing Sheets

QUANTITATIVE OPTOACOUSTIC TOMOGRAPHY FOR DYNAMIC ANGIOGRAPHY OF PERIPHERAL VASCULATURE

CROSS-REFERENCE TO RELATED APPLICATIONS

This application is a continuation-in-part under 35 U.S.C. § 120 of pending non-provisional application U.S. Ser. No. 13/748,563, filed Jan. 23, 2013 which claims benefit of priority under 35 U.S.C. § 119(e) of provisional application U.S. Ser. No. 61/632,389, filed Jan. 23, 2012, the entirety of both of which is hereby incorporated by reference.

BACKGROUND OF THE INVENTION

Field of the Invention

The present invention generally relates to the field of biomedical imaging and discloses the designs and methods used in quantitative optoacoustic tomography system that provides medically relevant information about disease of peripheral microvasculature based on measurements of functional parameters of the total hemoglobin and blood oxygen saturation using differential imaging of vasculature and microvasculature of live humans or animals measured at different ambient temperatures.

Description of the Related Art

Peripheral circulation, the distal functional unit of the cardiovascular system, provides exchange sites for gases, nutrients, metabolic wastes, and thermal energy between the blood and the tissues. Pathologic peripheral circulation reflects the breakdown of homeostasis in organisms, which ultimately leads to tissue inevitability (1). In vivo vascular imaging and characterization is of significant physiological, pathophysiological, and clinical importance. The visualization of peripheral vasculature may be useful in diagnostics and monitoring of various medical conditions, like vascular disorders, anatomical abnormalities, and obstructed blood flow (2-4). The examples include stenosis, thrombosis, embolism, frostbite, traumas, peripheral artery occlusive disease, Reynaud's syndrome, etc. The imaging of microcirculation and capillary networks is useful for the diagnosis of ischemia (5). The most important measurements of patho- and physiological effects comprise quantitative measurements of the functional parameters of vasculature and microvasculature include the total hemoglobin [tHb] and blood oxygen saturation [SO2]. These parameters measured under ischemia and hyperemia will enable early diagnostics of vascular diseases, such as cardiovascular disease, stroke, consequences of diabetes and other vascular and microvascular abnormalities. However, these measurements are not available today using the state of the art noninvasive imaging systems.

Another application of the vascular imaging could be related to the physiological stress test, used to study local vasomotor response. The stress tests involve changing environmental conditions (local occlusion, change of temperature, etc.) in order to bring certain physiological parameters, in this case the peripheral blood flow, close to extreme. Then, the environmental conditions are restored to normal, and the recovery of the individual's peripheral blood flow is monitored (6). Alternatively, the environmental conditions are kept under the stress for a prolonged time, while monitoring the adaptation of the local blood circulation. The patho- and physiologic effects of hypothermal stress are manifested in decreased blood flow caused by vasoconstriction, and reduced tissue metabolism, oxygen utilization, inflammation, and muscle spasm. For every one degree Celsius drop in body temperature, cellular metabolism slows by 5-7%. The patho- and physiologic effects of hyperthermal stress are manifested in increased blood flow caused by vasodilation, activation of tissue metabolism, oxygen utilization, inflammation, and muscle spasm (7).

There are many clinically applicable techniques for localized or systemic heating and cooling. Some of the most common involve the use of infrared lasers, focused ultrasound, microwave heating, induction heating, magnetic hyperthermia, infusion of warmed liquids, infrared sauna or direct application of heat such as through sitting in a hot room or wrapping a patient in hot blankets. Acquiring images of tissue throughout stages of response to physiologic stress may allow many conclusions to be made about local and systemic function. However, to ensure that these interpretations have both statistical significance and clinical value, an understanding of how normal physiology would behave within the imaging environment, under the stresses employed during a procedure, must be sought.

Currently, microangiography is performed by either MRI or CT (2,3). While these methods have been extensively explored, they have several drawbacks. CT angiography requires contrast agents to distinguish the vasculature. MRI scans are costly, and time required for MRI image acquisition about 30-50 minutes, is not optimal for dynamic monitoring of blood flow in real time, i.e. on short time scales.

The prior art describes optoacoustic (OA) imaging systems and photoacoustic microscopy systems as suitable for visualization of vasculature in live organisms (4-11). These systems are based on the acoustic signals generated by a short laser pulse absorbed within biological tissues (12). The OA imaging of blood vessels using near infrared (NIR) lasers may be effectively performed at depths up to several centimeters (13). At those laser wavelengths (700-900 nm) blood is 50 to 100 times more absorbing than the surrounding tissues (14), which eliminates the need for use of external optical contrast agents. However, the systems described in the prior art lack the capability of quantitative measurements of functional parameters in the vasculature and microvasculature throughout the entire volume of interest including deep vasculature. The existing systems of optoacoustic tomography (4) do not provide quantitative measurements of the functional parameters of [tHb] and [SO2] in the depth of the three-dimensional volumes of medical interest. The photoacoustic microscopy systems (5) lack the capability to image vasculature and measure functional parameters at depths greater than 1-2 mm, so that they provide insufficient value for medical diagnostics.

Thus, there is a need for improved methods for imaging of the peripheral vasculature and quantitative measurements of functional parameters with high temporal resolution. Specifically, the prior art is deficient in a system and method for dynamic optoacoustic imaging of peripheral vasculature. The present invention fulfills this longstanding need and desire in the art.

SUMMARY OF THE INVENTION

The present invention is directed to a system for quantitative optoacoustic tomography (qOAT) for dynamic angiography and differential measurements of functional parameters of the total hemoglobin [tHb] and blood oxygen saturation [SO2] obtained at different temperatures. An advanced OA imaging system disclosed here is a quantitative optoacoustic tomography (qOAT) system capable of rapid and accurate measurements of functional parameters of [tHb] and [SO2] at different temperatures. Imaging using qOAT system may be performed faster than physiologically revenant changes may occur in a live organism. Wang et al. (4) reported a 3 min 30 s acquisition time for optoacoustic images, which is much faster than MRI. The advanced system described below may be used to make partial view three-dimensional functional images in real time, i.e. video rate, and full view detailed quantitative differential functional images may be acquired within 20 sec. The present invention is also directed to a dynamic optoacoustic angiography method using qOAT system. The present invention is also directed to a related qOAT system further combined with anatomical ultrasound imaging of the volume of interest.

As an example of the qOAT system, provided herein is a system comprised of a specially designed short pulse laser operating in the wavelength cycling mode with at least two or more different wavelengths in the cycle, where these wavelengths are preferentially absorbed by hemoglobin and oxyhemoglobin within a visible and near-infrared spectral range. The wavelength cycling mode means that the wavelength of light emitted by a laser is changing with each next pulse of the laser. If the cycle contains two wavelengths, then it means that the two wavelengths are toggled. If the cycle contains three or more wavelengths, it means that each next laser pulse is emitted at a different wavelength and when three or more pulse of different wavelengths are emitted, the cycle is repeated again. The rapid cycling of two or more wavelengths is required for spatial coregistration of images obtained at different wavelengths, which means the spatial position of all voxels in the volume of interest remains the same, so that mathematical operations may be performed on those images. The images obtained at different temperatures also must be coregistered, if mathematical operations with these images are required for medical diagnostics. The laser output is connected with a fiberoptic light delivery system. The fiberoptic system for delivering optical energy to a volume of interest in a subject is designed with hot-fused input tip for maximum transmission and with randomized assembly of output fibers for making homogeneous illumination beam. The imaging system also comprises an imaging module operatively linked to the fiberoptic light delivery system. The imaging module comprises a vessel having a holder for supporting an appendage (such as a finger) therein, an optoacoustic coupling medium contained within the vessel and surrounding the appendage, and an array of ultrawide-band ultrasonic transducers configured to detect ultrasonic waves generated within the appendage upon delivery of the laser pulses thereto. The imaging system comprises a rotational and/or translational scanning system operatively linked to the imaging module configured for scanning the ultrasonic transducer array and the fiberoptic illumination system over the appendage. The ultrasonic transducer array and the fiberoptic bundle illumination system may be scanned independently (a preferred design for the full view 3D qOAT system) or the ultrasonic transducer array and the fiberoptic bundle illumination system may be combined in one housing (a preferred design for the partial vie 3D qOAT system). The imaging system comprises a computer controlled thermostat device for precision controlled rapid cooling or heating of the optoacoustic coupling medium and keeping the temperature constant during the scan of the image acquisition. This thermostat component may be placed inside the imaging module or be operatively linked to the imaging module and configured to rapidly achieve the desirable temperature in the optoacoustic coupling medium surrounding the subject of interest and thus affect physiological conditions of vasculature and microvasculature in the volume of interest. The imaging system comprises an electronics system comprising components for amplification, digitization and processing of the optoacoustic signals acquired from the ultrawide-band ultrasonic transducer array and a computer that has a memory, a central processor unit and a graphical processor unit and a high resolution display and is in electronic communication with the electronic components and is configured for system control and reconstruction of three-dimensional quantitative functional optoacoustic images of [tHb] and [SO2] acquired through the entire volume of interest at different temperatures. The present invention also is directed to a related dynamic optoacoustic angiographic imaging system further combined with an ultrasound imaging system for coregistered functional-anatomical imaging of the appendage.

The present invention also is directed to a method of quantitative optoacoustic tomography adopted to dynamic functional imaging of vasculature and microvasculature in an appendage of a subject. The method comprises positioning the appendage into the imaging module of the dynamic optoacoustic angiographic imaging system described herein and acquisition and reconstruction of quantitative optoacoustic images of functional parameters of vasculature and microvasculature at different temperatures of the optoacoustic coupling medium in the range from a cold temperature of about 15° C. to about 36° C. of normal physiological temperature to a hot temperature of about 42° C. An optoacoustic imaging scan of the appendage is performed at least at two different temperatures of the optoacoustic coupling medium, but preferentially at multiple temperatures within the range safely tolerable by the subject. The temperature of the optoacoustic coupling medium is changed in steps from the minimum to a maximum and quantitative optoacoustic tomography scan is performed at least at two rapidly cycling laser wavelengths in order to measure functional parameters of [tHb] and [SO2]. The key method for post-processing of acquired 3D optoacoustic images that enables quantitative measurement of functional parameters of [tHb] and [SO2] is the optical fluence normalization through the depth of the volume of interest. While experts in the art understand that the optical fluence attenuates as a function of the depth in tissue and, thus, must be normalized (equalized) at each of the wavelengths used for optoacoustic imaging in order to convert images of the absorbed optical energy into the quantitative images of the optical absorption coefficient (15), the present invention teaches an accurate and practical method for experimental measurements of the optical fluence distribution through the volume of the of interest by measuring the background absorbed optical energy as a function of depth on three-dimensional optoacoustic images. The qOAT system disclosed here is the only imaging system capable of experimental quantitative measurements of the background absorbed optical energy at each laser wavelength used to acquire 3D optoacoustic images. The enabling system component for quantitative optoacoustic tomography is the array of ultrawide-band ultrasonic transducers sensitive in the range of ultrasonic frequencies from at least 50 kHz (or less) to at least 8 MHz (or more). The ultrawide-band ultrasonic transducers provided herein for the purposes of quantitative optoacoustic tomography are different from well-known wide band (or broad band) ultrasonic transducers. For example, X Wang (23) and Y. Sudo (24) disclose wide band ultrasonic transducers with sensitivity enhanced in the high frequency range and adopted in their systems for the purposes of enhancing spatial resolution, we utilize ultrawide-band ultrasonic transducers with sensitivity enhanced in the low frequency range for the purposes of enhancing volumetric contrast of larger objects (such as major blood vessels) and enable capability of quantitative measurements of background absorbed optical energy as a function of depth and in turn enable optical fluence normalization through the volume of interest for quantitative optoacoustic tomography. The coregistered optoacoustic images acquired at multiple cycling wavelengths for each temperature of the optoacoustic coupling medium and differential functional images acquired at different temperatures are analyzed and processed and reveal whether vasculature of the subject of medical interest is functioning normally or abnormally. Variety of abnormalities in the spatial distribution of the vasculature and in the measured parameters of [tHb] and [SO2] demonstrate the presence of various abnormal heath conditions.

The present invention is directed further to a related method further comprising displaying differential images of functional parameters of [tHb] and [SO2] in peripheral vasculature deep through in the appendage as a function of time and temperature determined from the dynamic optoacoustic angiographic scans of the appendage and diagnosing a medical condition of the appendage or the peripheral vascular system of the subject based on the displayed differential functional images and quantitative functional parameters. The present invention is directed to another related method further comprising performing ultrasonic imaging of the appendage and displaying coregistered functional maps within anatomical structures.

Other and further aspects, features, and advantages of the present invention will be apparent from the following description of the presently preferred embodiments of the invention given for the purpose of disclosure.

BRIEF DESCRIPTIONS OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "optoacoustic imaging" refers to imaging based on optically induced acoustic signals and also is referred to as photoacoustic imaging or thermoacoustic imaging.

As used herein, the term "computer" or "computer system" refers to any networkable tabletop or handheld electronic device comprising a memory, a processor, a display and at least one wired or wireless network connection. As is known in the art, the processor is configured to execute instructions comprising any software programs or applications or processes tangibly stored in computer memory or tangibly stored in any known computer-readable medium.

As used herein, the term "subject" refers to a human or other mammal or animal or to any portion or body part thereof on which imaging, for example, any optoacoustic imaging, as described herein, may be performed.

In one embodiment of the present invention there is provided a quantitative optoacoustic tomography system for dynamic angiography comprising: a pulsed laser for delivering optical energy to a volume of interest on a subject at least at two rapidly cycling wavelengths preferentially absorbed by hemoglobin and oxyhemoglobin, a fiberoptic bundle light delivery system with randomized fibers for illumination of the entire imaging the volume of interest, an imaging module filled optoacoustic coupling medium at precisely controlled temperature in the range of temperatures of at least 12 deg C. to 45 deg C. tolerable by the subject, an array of ultrawide-band ultrasonic transducers with desirably equal sensitivity over a range of ultrasonic frequencies of at least 50 kHz to 15 MHz for detection of optoacoustic signals with high resolution and without distortions of quantitative volumetric contrast, a circulation system for the optoacoustic coupling medium providing thermostat regulated by a computer and capable of rapid cooling and heating of the coupling medium and keeping it at a constant temperature, a multichannel electronic data acquisition system with ultrawide-band analog amplifiers, analog-to-digital converters, memory, and field programmable gate array microprocessor for signal processing, storage and transmission to a computer, a computer with multicore CPU and multicore GPU and software for system control and for reconstruction and processing of three-dimensional quantitative tomography images of functional parameters of the total hemoglobin and blood oxygen saturation measured at different physiological temperatures for purposes of dynamic angiography of the volume of interest, and a high resolution display for presentation of three-dimensional angiographic images of the volume of interest, 2D slices through the volume of interest and quantitative values of the functional parameters of vasculature and microvasculature.

Further to this embodiment the optoacoustic imaging system for dynamic angiography is combined with ultrasound imaging of the volume to display coregistered functional-anatomical maps. These maps present quantitative functional parameters of [tHb] and [SO2] within ultrasonically displayed anatomic structures. In this further embodiment the ultrasound may be electrically generated or may be laser generated. In all embodiments the volume of interest in the subject may be an appendage.

In both embodiments the means for delivering optical energy may comprise a short pulse laser operable at two or more cycling wavelengths and a fiberoptic delivery system optically connected to the laser. Particularly, those at least two wavelengths are selected from 757±5 nm and 845±5 nm and additional wavelengths comprise the visible and near-infrared spectrum, wherein specific wavelengths are selected for preferential absorption by hemoglobin and oxyhemoglobin or isosbestic point 800±5 nm of equal absorption by hemoglobin and oxyhemoglobin. Cycling wavelengths means that the laser emits each next pulse with a different wavelength. The cycle has a minimum of two wavelength, but three or more wavelengths may be included in the cycle. Rapid cycling is important for spatial coregistration of optoacoustic images obtained at each wavelength, so that these images are mathematically processed to produce quantitative functional images of the total hemoglobin and blood oxygen saturation.

Also in both embodiments the imaging module is the main component for imaging the extremity over a range of temperatures. The imaging module may comprise a vessel shaped to receive the volume of interest, an optoacoustic coupling medium contained in the vessel transparent for light and conducting ultrasound without losses. It is important for dynamic angiography system to comprise a device, such as thermostat, for user controlled rapid temperature change in the optoacoustic coupling medium, precise temperature stabilization and regulation. Such thermostat can be included in the imaging module or be part of the circulation system connected with the imaging module by tubes (pipes). Imaging module also contains an array of ultrasonic transducers configured to detect ultrasonic waves generated within the volume of interest upon delivery of the optical pulses therein and a scanner operatively connected with the imaging module to scan the array ultrasonic transducers over the area of interest. A fiberoptic light delivery system is placed in one housing with the array of ultrasonic transducers or be a bundle of fibers in a separate housing. Particularly, the scanner may operate in rotational mode or translational mode or a combination thereof and the one or more ultrasonic transducers may comprise a transducer array. In case when an array of ultrasonic transducer and a fiberoptic bundle are separate, they may be scanned separately and independently from each other, so that full illumination of the volume of interest can be achieved for each position of the ultrasonic transducer array.

In addition in both embodiments the qOAT system for three-dimensional angiographic images includes electronic components operatively linked to the array of ultrasonic transducers configured for acquisition of optoacoustic signals, signal and/or image processing and data transmission to a computer and a computer, having a memory, a processor and a display, that is in electronic communication with the electronic components and configured for system control and three-dimensional and two-dimensional optoacoustic image visualization. Particularly, the signal or image processing by electronic components comprises one or more processes that are signal amplification, digitization, filtering, deconvolution, backprojection, reconstruction, optical fluence normalization, image summation, inversion, transformation, or iteration.

In another embodiment of the present invention there is provided a dynamic optoacoustic angiographic imaging system operating in real time i.e. faster than significant physiological changes can occur in the subject of diagnostic interest. This system comprises a) a short pulse laser operable at two wavelengths within a visible and near-infrared spectral range where one wavelength is preferentially absorbed by red blood cells and the second wavelength is preferentially absorbed by a substance of medical interest (such as a drug or diagnostic or therapeutic agent) exogenously injected in the blood of a subject; b) a fiberoptic laser light delivery system comprising bundles of randomized fibers operatively linked to the laser; c) an imaging module operatively linked to the fiber optic laser light delivery system, where the imaging module comprises a vessel having means for supporting an appendage therein; an optoacoustic coupling medium contained within the vessel and covering the appendage, a user controlled (computer controlled) thermostat for rapid and precision cooling or heating of the coupling medium and stabilization of temperature of the coupling medium; and an array of ultrasonic transducers configured to detect ultrasonic waves generated within the appendage upon delivery of the laser light thereto; d) a rotational and/or translational scanning system operatively linked to the imaging module configured for scanning the ultrasonic transducer array over the appendage; e) an electronics system comprising components for amplification, digitization and processing of the optoacoustic signals acquired from the ultrasonic transducer array; and f) a computer, having a memory, a processor and a display, in electronic communication with the electronic components and configured for visualization of three-dimensional and two-dimensional optoacoustic images and presentation of quantitative parameters relevant to specific health conditions.

In a further embodiment the dynamic optoacoustic angiographic imaging system combines a system for ultrasound imaging of the appendage for display of functional maps inside anatomical structures. In this ultrasound imaging system the ultrasound may be electrically generated or may be laser generated. In both embodiments the means for supporting the appendage may comprise a bracket.

In yet another embodiment of the present invention there is provided a method for quantitative optoacoustic tomography applied to assess conditions of vasculature and microvasculature of a subject using dynamic angiography of an appendage. The method comprises the steps of a) stabilizing the optoacoustic coupling medium contained within the imaging module at a normal physiological temperature for the subject; b) positioning the appendage into the imaging module; c) performing an optoacoustic imaging scan of the appendage at the normal physiological temperature at two or more cycling laser wavelengths; d) rapidly changing the temperature of the optoacoustic coupling medium in steps from the normal to a maximum or minimum safe temperature safely tolerable by the subject; e) performing an optoacoustic imaging scan at each step of changed and then stabilized temperature in the range from the maximum (about 42° C.) to the minimum (about 15° C.) safely tolerable by humans; f) saving, analyzing and processing optoacoustic signals acquired at each step corresponding to a specific temperature; and g) reconstructing two or more spatially coregistered three-dimensional optoacoustic images corresponding to two or more different laser wavelengths, make these images reconstructed for each step of the temperature of the optoacoustic coupling medium; h) performing optical fluence normalization (equalization) on the surface of the appendage and through the depth of the entire volume of interest for each laser wavelength used for imaging thus making these images quantitatively accurate; i) performing mathematical operations with the quantitative images and displaying the images of functional parameters in the volume of interest.

Further to this embodiment the method comprises j) displaying differential optoacoustic images of the functional diagnostic parameters as they change over time and as a function of temperature; and k) diagnosing a medical condition of the subject or the state of vascular and microvascular systems of the subject based on the displayed functional images and diagnostic parameters. In this further embodiment anatomical and functional details of the peripheral vasculature may characterize thermoregulatory response and other mechanisms responsible for vasomotor activity. In another further embodiment the method comprises performing ultrasonic imaging of the appendage. In all these embodiments the appendage is an arm, a hand, fingers, a leg, a foot, or toes.

In yet another embodiment of the present invention there is provided a quantitative optoacoustic tomography system for dynamic angiography of functional parameters in a subject comprising a pulsed laser operating in a wavelength cycling mode with at least two wavelengths in the cycle preferentially absorbed by hemoglobin and oxyhemoglobin; a fiberoptic bundle light delivery system with randomized fibers to provide a homogeneous illumination beam for delivery of the optical energy to the entire volume of interest in the subject; an imaging module filled with an optoacoustic coupling medium at a precisely controlled temperature from a range of at least 12° C. to 45° C. tolerable by the subject; an array of ultrawide-band ultrasonic transducers with a desirably equal sensitivity over a range of ultrasonic frequencies of at least 50 kHz to 15 MHz for detection of optoacoustic signals with high resolution and without distortions of quantitative volumetric contrast; a circulation system in fluid communication with the optoacoustic coupling medium comprising a thermostat regulated by a computer and configured to cool and heat the optoacoustic coupling medium and to maintain the optoacoustic coupling medium at a constant temperature; a multichannel electronic data acquisition system with ultrawide-band analog amplifiers, analog-to-digital converters, a memory, and a field programmable gate array microprocessor for signal processing, storage and transmission to a computer; a computer with a multicore CPU and a multicore GPU and software configured for system control, for regulation of the thermostat and for reconstruction and processing of three-dimensional quantitative tomography images of the functional diagnostic parameters measured at different physiological temperatures for dynamic angiography of the volume of interest; and a high resolution display in electronic communication with the computer and configured for presentation of three-dimensional angiographic images of the volume of interest, 2D slices through the volume of interest or quantitative values of the functional parameters of vasculature and microvasculature or a combination thereof.

Further to this embodiment the optoacoustic imaging system comprises an ultrasound imaging system configured for coregistration of functional images and anatomical images of the volume of interest. In this further embodiment the ultrasound may be electrically generated or laser generated.

In both embodiments of the optoacoustic imaging system the at least two cycling wavelengths may comprise the visible spectrum and the near-infrared spectrum. In one aspect of both embodiments the at least two cycling wavelengths may be 757±5 nm and 845±5 nm. In another aspect the at least two cycling wavelengths may comprise at least the isosbestic point wavelength of 800±5 nm of equal absorption by hemoglobin and oxyhemoglobin.

Also in both embodiments the functional diagnostic parameters may be total hemoglobin and blood oxygen saturation. Alternatively, in both embodiments the functional diagnostic parameters may be concentrations of exogenously administered diagnostic, therapeutic or contrast agents. In addition the array of ultrawide-band ultrasonic transducers may be scannable about the volume of interest in a rotational mode or a translational mode or a combination thereof. Furthermore, the volume of interest may be an appendage of the subject. In all embodiments and aspects thereof the system may be configured to evaluate blood flow, ischemia, hyperemia, or to assist in an administration of hemodialysis.

In yet another embodiment of the present invention there is provided a method for quantitative optoacoustic tomography to assess conditions of vasculature and microvasculature in a subject using dynamic angiography of an appendage, comprising the steps of a) stabilizing an optoacoustic coupling medium contained within an imaging module at a normal physiological temperature for the subject; b) positioning the appendage into the imaging module; c) performing an optoacoustic imaging scan of the appendage at the normal physiological temperature with at least two cycling laser wavelengths; d) rapidly changing the temperature of the optoacoustic coupling medium in steps from the normal physiological temperature to a maximum safe temperature of about 42° C. or to a minimum safe temperature of about 15° C. safely tolerable by the subject; e) performing an optoacoustic imaging scan at each step of changing the physiological temperature and then at a stabilized temperature in a range from the maximum safe temperature to the minimum safe temperature of the optoacoustic coupling medium; f) saving, analyzing and processing optoacoustic signals acquired at each step of changing the temperature; g) reconstructing two or more spatially coregistered three-dimensional optoacoustic images corresponding to the at least two cycling laser wavelengths at each step of changing the temperature of the optoacoustic coupling medium; h) performing an optical fluence normalization or equalization on the surface of the appendage and through a depth of the entire volume of interest for each laser wavelength used for imaging thereby making these images quantitatively accurate; i) performing mathematical operations on the quantitative images; and j) displaying the images of functional and anatomical parameters in the volume of interest. Further to this embodiment, the method comprises j) displaying differential optoacoustic images of the functional diagnostic parameters as they change over time and as a function of temperature; and k) diagnosing a medical condition of the subject or a state of vascular and microvascular systems of the subject based on the displayed images of the functional diagnostic parameters.

In both embodiments functional and anatomical details of the peripheral vasculature may characterize a thermoregulatory response and other mechanisms responsible for vasomotor activity. Also in both embodiments the appendage is an arm, a hand, fingers, a leg, a foot, or toes.

In yet another embodiment of the present invention there is provided a optoacoustic imaging system for dynamic angiography comprising means for delivering optical energy to a volume of interest on a subject; means for imaging the volume of interest over a range of temperatures tolerable by the subject; and means for producing two- or three-dimensional angiographic images of the volume of interest. In a further embodiment the optoacoustic imaging system for dynamic angiography comprises means for ultrasound imaging of the volume. In this further embodiment the ultrasound may be electrically generated or may be laser generated. In all embodiments the volume of interest in the subject may be an appendage.

In both embodiments the means for delivering optical energy may comprise a short pulse laser operable at one or more wavelengths and a fiberoptic delivery system optically connected to the laser. Particularly the one or more wavelengths may comprise the visible and near-infrared spectrum where spectral bands are deliverable in a sequence or toggled.

Also in both embodiments the means for imaging the extremity over a range of temperatures may comprise an imaging module having a vessel shaped to receive the volume of interest, an optoacoustic coupling medium contained in the vessel, means for temperature regulation of the coupling medium, and one or more ultrasonic transducers configured to detect ultrasonic waves generated within the volume of interest upon delivery of the optical energy therein and a scanner operatively connected with the imaging module to scan the one or more ultrasonic transducers over the area of interest. Particularly, the scanner may operate in rotational mode or translational mode or a combination thereof and the one or more ultrasonic transducers may comprise a transducer array.

In addition in both embodiments the means for producing two- or three-dimensional angiographic images may comprise electronic components operatively linked to the one or more ultrasonic transducers configured for acquisition of optoacoustic signals, signal and/or image processing and data transmission to a computer and a computer, having a memory, a processor and a display, that is in electronic communication with the electronic components and configured for system control and three-dimensional and two-dimensional optoacoustic image visualization. Particularly, the signal or image processing by electronic components comprises one or more processes that are signal amplification, digitization, filtering, convolution or deconvolution, backprojection, reconstruction, summation, inversion, transformation, or iteration.

In yet another embodiment of the present invention there is provided a dynamic optoacoustic angiographic imaging system, comprising a) a short pulse laser operable at one or more wavelengths within a visible and near-infrared spectral range; b) a fiberoptic laser light delivery system comprising bundles of randomized fibers operatively linked to the laser; c) an imaging module operatively linked to the fiber optic laser light delivery system, where the imaging module comprises a vessel having means for supporting an appendage therein; an optoacoustic coupling medium contained within the vessel and covering the appendage, means for precision controlled cooling or heating of the coupling medium; and an array of ultrasonic transducers configured to detect ultrasonic waves generated within the appendage upon delivery of the laser light thereto; d) a rotational and/or translational scanning system operatively linked to the imaging module configured for scanning the ultrasonic transducer array over the appendage; e) an electronics system comprising components for amplification, digitization and processing of the optoacoustic signals acquired from the ultrasonic transducer array; and f) a computer, having a memory, a processor and a display, in electronic communication with the electronic components and configured for system control and three-dimensional and two-dimensional optoacoustic image visualization.

Further to this embodiment the dynamic optoacoustic angiographic imaging system comprises a system for ultrasound imaging of the appendage. In this ultrasound imaging system the ultrasound may be electrically generated or may be laser generated. In both embodiments the means for supporting the appendage may comprise a bracket.

In yet another embodiment of the present invention there is provided a method for optoacoustic imaging of an appendage of a subject, comprising the steps of a) heating the optoacoustic coupling medium contained within the imaging module comprising the dynamic optoacoustic angiographic imaging system as described supra to a normal physiological temperature for the subject; b) positioning the appendage into the imaging module; c) performing an optoacoustic imaging scan of the appendage at the normal temperature; d) changing the temperature of the optoacoustic coupling medium in steps from the normal to a maximum or minimum safe temperature safely tolerable by the subject; e) performing an optoacoustic imaging scan at the maximum or minimum safely tolerable temperature; f) analyzing and processing optoacoustic signals acquired at both the normal and the maximum or minimum safely tolerable temperatures; and g) reconstructing two- or three-dimensional optoacoustic images from the analyzed signals.

Further to this embodiment the method comprises h) displaying differential anatomical images of peripheral vasculature in the appendage and functional diagnostic parameters as a function of time and temperature determined from the dynamic optoacoustic angiographic scan of the appendage; and i) diagnosing a medical condition of the appendage or the peripheral vascular system of the subject based on the displayed functional images and diagnostic parameters. In this further embodiment anatomical and functional details of the peripheral vasculature may characterize thermoregulatory response and other mechanisms responsible for vasomotor activity. In another further embodiment the method comprises performing ultrasonic imaging of the appendage. In all these embodiments the appendage is an arm, a hand, fingers, a leg, a foot, or toes.

Provided herein is a novel laser optoacoustic imaging system (QOAT) and method for dynamic micro-angiography intended for in vivo vascular imaging of human (animal in general) extremities. The system employs an optoacoustic detector (preferred detector is an array of ultrawide-band ultrasonic transducers) that collects optoacoustic signals around the said extremity (e.g. finger, toe, etc.) providing optoacoustic data necessary for tomographic reconstruction of the three-dimensional images. A near-infrared Q-switched laser is used to generate optoacoustic signals with increased contrast for blood vessels. The laser is coupled through randomized fiberoptic bundles (preferred orientation of illumination is in orthogonal relative to the detector.

This optoacoustic imaging system may be used for diagnostics of various medical conditions that are manifested in change of the peripheral microvasculature in blood flow through extremities. Examples of the medical conditions that could be diagnosed and staged using the QOAT include the cardiovascular disease, atherosclerosis, peripheral arterial disease (PAD), diabetic angiopathy, thrombosis, frostbite, and traumas.

Optoacoustic technology has several unique qualities that make it an ideal candidate for integrating physiologic assessment of the circulation with medical imaging. The use of pulsed, near infrared light at powers intended for imaging delivers enough energy to produce an optoacoustic response from light absorption at the molecular level but does not trigger any sensory or systemic responses in the testing subject. In addition, the conditions under which optoacoustic imaging may be performed are very flexible; a testing subject may be imaged in a ventilated room, submerged in water, coated with gels, all at varying temperatures and pressure without inhibiting the imaging mechanics or basic function. The multiplicity of conditions that may be freely employed in optoacoustic imaging may yield great freedom for determining the viability and status of functional tissue.

It is important to observe that changes in peripheral blood perfusion have two primary components: variable arteriole diameter and arteriovenous anastomotic flow. Arteriole diameter is heavily influenced by cardiovascular function and under direct control by the sympathetic nervous system, sensory pathway, and endocrine system. Many variables such as temperature, blood volume, chemical concentrations, and pressure may affect the mechanisms of vasomotor control to promote adaptive vascular changes. The resulting effect either constricts or dilates the arterioles, resulting in both systemic and local changes in the perfusion of tissue. Arteriovenous anastomoses are present throughout the body and have great significance in regards to perfusion during periods of stress, compromised function, or heightened activity.

One type of anastomosis of particular importance is the capillary networks that branch from arterioles in the periphery and viscera. These microscopic networks are the primary sites of nutrient and water exchange between plasma and intracellular fluid, but also have major roles in mediating the effects of vasomotor control. It is important to observe that all capillary arteriovenous anastomoses do not have blood flowing through them at all times. Changes in the many variables affecting vasomotor controls alter the perfusion of these networks. Taken together, arteriovenous anastomoses and arterioles present a very intimate link to the overall homeostasis of an individual.

Using wavelengths of light between 700 nm and 1100 nm the optoacoustic imaging is optimized for visualization of the peripheral vasculature. The resulting images produce strong definitions of individual blood vessels, providing the information on varying diameter, branching, and tissue density. The amount of optoacoustic signal generated in tissue depends primarily on the concentration of absorbing species per voxel, here blood, and the amount of light delivered. Assuming a constant amount of light is available, any changes in the magnitude of optoacoustic response from tissue may be attributed to an increase in the concentration blood in tissue, or increased perfusion. The following embodiment of assessing physiology through imaging will outline one of the functions of vasomotor control, biphasic vasodilation in response to hyperthermia.

Vasomotor Control Assessment: Hyperthermia-Induced Activation of Biphasic Vasodilation A sustained, local hyperthermic stimulus produces a biphasic thermoregulatory response. The biphasic response is composed of fast and delayed mechanisms. The fast response is mediated by the release of CGRP, substance P, and neurokinin from stimulated C-fiber afferent nerves to produce the perception of heat and vasodilation. The fast response initiates a rise in superficial blood flow for approximately 3-5 minutes following sustained heat stimulation. The receptors involved are sensitive to temperatures of 39° C. or greater, but heat perception and the active vasodilation mechanism may have sensitivities down to 29° C., although at the lower end of this range, vasodilation may compete with vasoconstriction tone and be indistinguishable.

The delayed response is mediated by nitric oxide vasodilation. Persistent stimulation beyond the 5 minutes will activate the nitric oxide vasodilatory pathway in order to produce a steady-state exchange of heat across the heated region of skin. Maximal vasodilatory responses occur around 42° C. and require 25-30 minutes to reach steady-state in healthy individuals. Following the fast mechanism, a decline in vasodilation will occur before the delayed response assumes control and climbs to steady-state.

The assessment of vasomotor control should consider the implications of involving the sympathetic nervous system, the sensory pathway, endocrine system, and cardiovascular function. It is also important to observe that the mechanisms of sudomotor control, vasoconstriction, and vasodilation are intimately associated and may produce combined effects following thermo-stimulation. The specific mode of observing vasodilation should produce a specific, localized response to prevent combined thermoregulatory activity. For this assessment, the index finger will be subjected to superficial heat stress while imaged with optoacoustic methods to observe vasodilation. The finger is an ideal candidate as it contains both glabrous and non-glabrous skin on its palmar and dorsal aspects, respectively.

Glabrous skin is known to distinctly lack active vasodilation and may produce vasodilation only via the reduction of sympathetic tone, which produces vasoconstriction, or the release of nitric oxide. Nonglabrous skin does contain active vasodilation and should show the fast mechanism associated with active vasodilation. The following procedure for assessment of hyperthermia-induced activation of biphasic vasodilation is intended to be performed on the index finger within an optoacoustic imaging environment.

Particularly the instant invention demonstrates or provides the following:

Assessment of Hyperthermia-Induced Activation of Biphasic Vasodilation

1. Submerge the region of interest into an imaging environment heated to approximately 25° C. to ensure vasoconstriction is active but without heavy tone. Ensure a comfortable temperature and proper seating for the patient during the scan to prevent activation of extraneous thermoregulatory mechanisms or uncontrolled deviations in sympathetic tone.
2. Image the entire region of interest, taking care to constrain the finger location within the imaging module.
3. Quickly (in 1 minute or less) heat the imaging environment to 40° C. Sustain this temperature until otherwise directed.
4. Once the imaging environment reaches 40° C., immediately begin a second scan to image the entire region of interest. This marks the time of 0, where hyperthermic stimulation begins.
5. Continuously image the entire region of interest for 10 minutes.
6. Wait 5 minutes. At fifteen minutes, image the entire region of interest again.
7. Wait 10 minutes. At 25 minutes, image the entire region of interest again.
8. Finish the hyperthermic stimulation. Quickly reduce the temperature of the imaging environment to 25° C. (in 1 minute or less).
9. Once the imaging environment reaches 25° C., image the entire region of interest again.

Systemic Sclerosis and Raynaud's Syndrome

Systemic sclerosis, or scleroderma, is a disease resulting from autoimmune destruction of healthy connective tissue throughout the body, including blood vessels and skin. Microangiopathy, affecting the capillary arteriovenous networks, is a primary feature and can be detected early in the course of disease. It is important whether observed symptoms are indeed indicative of systemic sclerosis or due to another disease process.

Raynaud's phenomenon, for example, is a disorder of vasoconstriction frequently involved with systemic sclerosis. Raynaud's can manifest as either a primary condition or secondary to disease such as systemic sclerosis. Distinguishing between the two forms can be difficult as the presentations are similar. In primary Raynaud's, resting hand perfusion is generally very low compared with the early stages of scleroderma, but the distinguishing factor between the two is the response to thermal stress. Specifically, applying hypothermic conditions to a primary Raynaud's subject will result in a rapid loss of perfusion with sustained losses long after restoring temperature to comfortable levels. In systemic sclerosis, the apparent Raynaud's will not have such a profound loss of perfusion and will recover much more quickly after removal of the hypothermic stress.

Considering the protocol for assessment of hyperthermia-induced activation of biphasic vasodilation, it is contemplated that methods may be designed that implement hypothermia to activate vasoconstriction. Arteriole constriction, in contrast to dilation, is constantly active and holds a baseline tone which affects both perfusion of distal branches and blood pressure. Hypothermia generates a heightened level of vasoconstriction to prevent excessive loss of core heat. In primary Raynaud's, the sympathetic tone which defines the level of vasoconstriction is pathologically increased. Systemic sclerosis differs in that the observed loss of perfusion is primarily due to vascular damage.

Vasomotor Control Assessment: Hypothermia-Induced Activation of Vasoconstriction Other possible thermal stress tests to assess complex aspects of vasomotor control of local temperature include cooling the subject and then heating the subject.

Image Reconstruction

Continuous 3D imaging with multiple full 360-degree rotations enables implementation of the continuous time-averaged image reconstruction procedure. The procedure involves tomographic reconstruction of the full 360-degree scans sequentially shifted by a single or multiple steps of the rotational motor. The reconstructed 3D images or individual sections of 3D images then form a sequence of frames for the optoacoustic 3D or 2D movie showing the dynamic optoacoustic angiography.

Quantitative Optoacoustic Tomography for Dynamic Angiography of Peripheral Vasculature The present invention demonstrates that it is crucial that the frame rate of the created 3D or 2D optoacoustic movie is standardized by a specific compression ratio with respect to the real frame rate achieved at the moment of angiography procedure. That condition is essential so that all the created optoacoustic movies will be perceived by the doctors in the same manner and could be compared visually across different patients/procedures.

Spatial Separation of the Microvasculature

The present invention demonstrates a method of spatial separation of the microvasculature and larger peripheral blood vessels for an enhanced diagnostic evaluation. Microvascular networks have different thermal regulation than larger blood vessels. Therefore, they if possible should be separated in optoacoustic images/movies from their larger counterparts. The method of separation may include using optoacoustic transducers with different impulse responses to measure signals from microvasculature and larger vessels. It also may include application of an analog or digital filter to the data already measured by the array of optoacoustic transducers. Lastly, the optoacoustic images/movies can be reconstructed/created and then spatially filtered to get separate information on temporal and spatial behavior of microvasculature and larger vessels during the stress test. The general approach includes retaining lower frequency components for larger blood vessels and higher frequency components for microvasculature.

Functional Diagnostic Parameters of a Dynamic OA Angiography

Functional diagnostic parameters of dynamic OA angiography are defined separately for microvasculature and larger blood vessels. Visualized extremity/organ is also divided into subsections/compartments, i.e., finger, for example, can be divided into three subsections corresponding to the phalanxes. Then the functional diagnostic parameters are: (a) For each subsection cumulative OA intensity is normalized to its own maximum and is plotted as a function of time. This parameter defines how the visualized subsection or the entire organ is perfused with time. (b) For each subsection cumulative OA intensity is normalized to the OA intensity of the entire organ, and is plotted as a function of time. This parameter tracks spatial distribution of blood as a function of time.

qOAT by Normalization of the Optical Fluence as a Function of Depth

The main merit of the dynamic optoacoustic angiography is the capability to provide quantitative information of functional parameters of [tHb] and [SO2] in vasculature and microvasculature. It is not possible to avoid optical attenuation of near-infrared light in human tissues, which results in a gradient of the effective optical fluence into the depth of tissue defined by the effective optical attenuation. The brightness of background microvasculature with diameters much smaller than the spatial resolution of qOAT system provides information of the effective optical fluence through the volume of interest.

In order to reconstruct volumetric images with brightness independent of the depth from the illuminated surface, brightness of voxels is exponentially increased in the radial directions form the skin surface along the radial direction into the depth. Ultrawide band ultrasound transducers enable detection of lower ultrasonic frequencies and thus visualize the background absorbed optical energy. This, in turn, enables direct measurements of the effective optical attenuation on each optoacoustic image acquired at different wavelengths and different temperatures. The measured effective optical attenuation in an adult finger at 757 nm was found to be approximately $u_{\it eff}$~1.2 cm$^{-1}$ and slightly smaller number $u_{\it eff}$~1.17 cm$^{-1}$ was measured at the wavelength of 800 nm. The exponential function $\exp(u_{\it eff}R)$ was applied to the brightness palette of the optoacoustic images, where R is the depth in tissue along the radial direction. This approach was permitted reconstruction of functional images of [sO2] showing either oxygenated blood in red or deoxygenated blood in blue with brightness proportional to the [tHb].

Applications of qOAT

It is demonstrated that pathologies associated with vasomotor control are numerous and it is plausible that any pathological state can have some effect. However, the process of establishing the assessment of physiology in imaging should begin with defining how its methods may provide diagnostic or preventative benefit. Building off examples of pathologies that have a strong component of physiologic stress or compromise, which can be assessed using the methods provided here, will both serve to outline the potential of this technology and focus the "window" utilized for diagnosis. Further methods and applications of the optoacoustic imaging under hypothermal/hyperthermal stress are described.

It is demonstrated that the thermoregulatory response and other physiological effects regulated via vasomotor activity could be studied by repetitive three-dimensional optoacoustic imaging following the stress test that modifies the finger blood flow. Future improvements to the stabilization of the finger during the scans will provide less motion artifacts, better resolution and contrast of individual optoacoustic images, which is essential for quantitative differential image analysis and accurate calculation of functional diagnostic parameters. The speed of each scan may be increased to enable uninterrupted multiple scanning, which enables the study of the faster processes that happen as a result of vasomotor activity.

One skilled in the art of optoacoustic imaging can recognize that such dynamic optoacoustic angiography may be performed in real-time with the invented laser optoacoustic imaging system (QOAT). Scanning of the probe enables one to locate and track arteries and veins of a human forearm in real-time. This system can be modified to provide fast preoperative mapping of forearm vessels necessary for establishment of hemodialysis. Also, the frame-by-frame analysis of the recorded QOAT images in a real time movie mode may be used to measure dynamic changes of the cross-section of the arteries. If combined with the Doppler ultrasound, real-time optoacoustic information on the change of the blood vessel cross-section provided by QOAT could be used in estimation of the instantaneous local blood flow rates. Such a localized high resolution analysis of vascular dynamics is superior to traditionally used plethysmography, which provides blood flow information only within a thick segment of the extremity without spatial resolution. Such data would be useful in tests aimed to estimate the physiological response of the peripheral circulatory system to different types of stress, like thermoregulatory mechanisms, vascular effects of the drugs and in diagnosing of local ischemia.

The profile of variations in arterial diameter clearly indicate a cyclical increase and decrease in blood volume that likely reflects the pulsatile nature of arterial blood flow during systole and diastole. This suggests that a real-time optoacoustic system can be potentially used, similarly to plethysmography, for monitoring arterial blood flow during the cardiac cycle and for characterizing properties of vascular wall function, such as elasticity, endothelial function (vascular reactivity), and augmentation index. Clinical conditions that would benefit from such analysis include atherosclerotic peripheral arterial disease, veno-occlusive disease, and venous valvular insufficiency.

As described below, the invention provides a number of advantages and uses, however such advantages and uses are not limited by such description. Embodiments of the present invention are better illustrated with reference to the Figure (s), however, such reference is not meant to limit the present invention in any fashion. The embodiments and variations described in detail herein are to be interpreted by the appended claims and equivalents thereof.

Figure 1A:
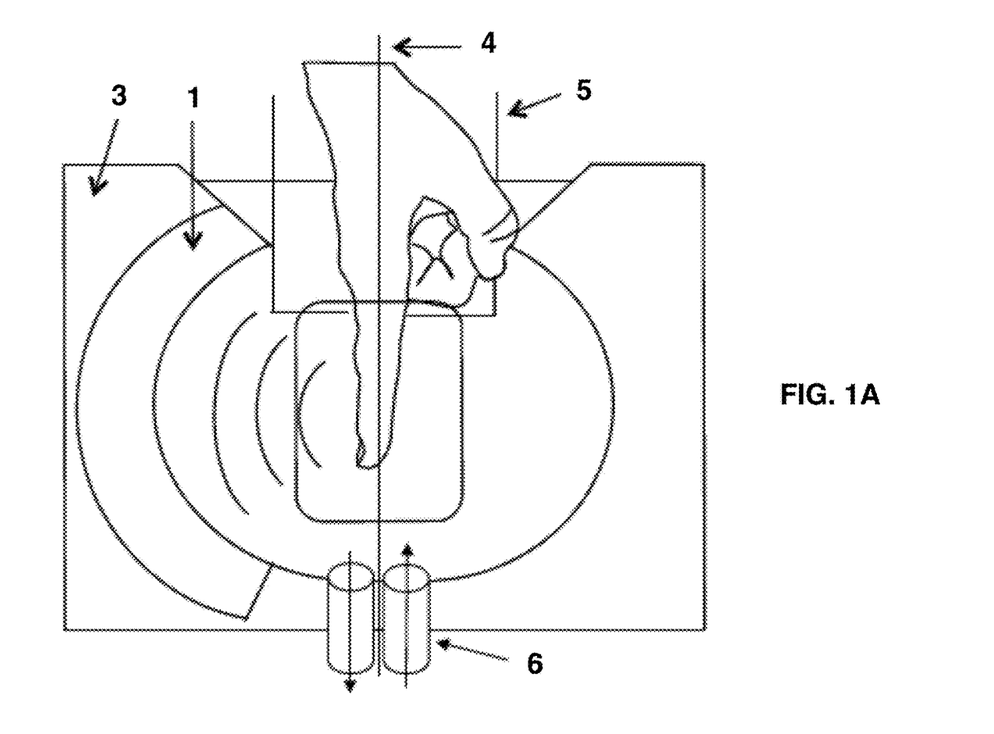
FIGS. 1A-1B are a schematic of the imaging module component of the three-dimensional dynamic optoacoustic microangiography system (QOAT) in a side cross-sectional view (FIG. 1A) and a bottom view (FIG. 1B).
Figure 1B:
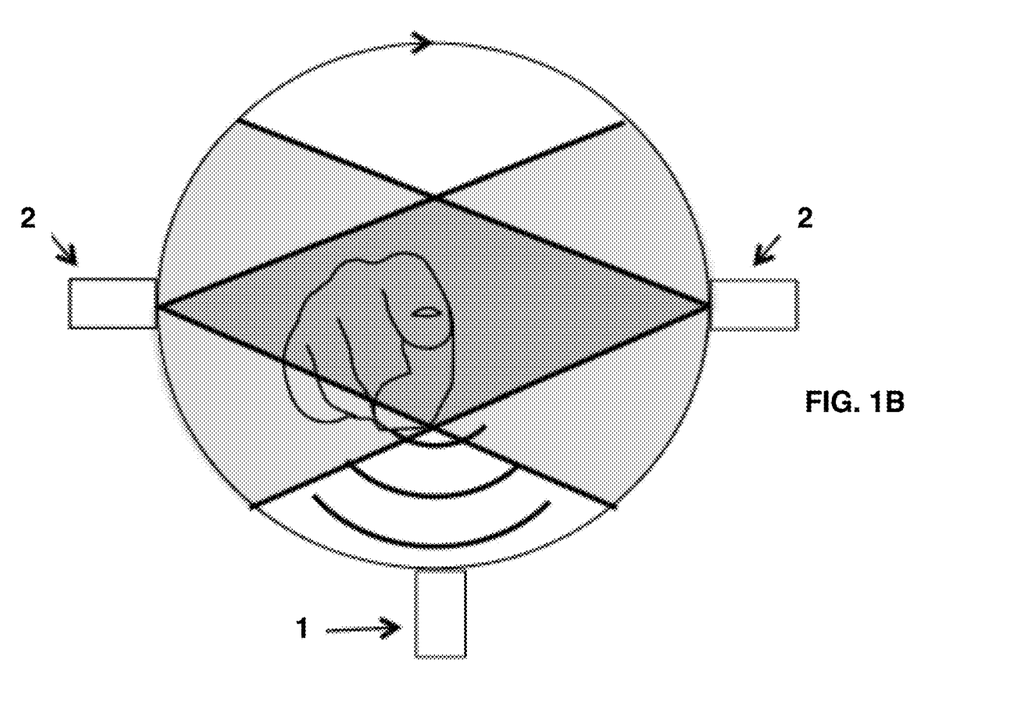

FIGS. 1A-1B represent an illustration of the imaging module component of the three-dimensional optoacoustic microangiography system (qOAT). The qOAT imaging module comprises an acoustic array probe 1, laser fiberoptic bundles 2 for illumination of the volume of interest (left and right); a scanning chamber or bowl 3, and a hand bracket 4. A hand 5 of a human subject (with finger as the volume of interest) is positioned within the scanning chamber and held in place by the bracket. A circulation system is represented by a pair of pipes 6 supplying and draining the optoacoustic coupling medium at thermostatic temperature controlled by a computer.

The three-dimensional optoacoustic microangiography system is configured to acquire signals in orthogonal and backward modes of optical illumination. The qOAT system utilizes an array of ultrawide-band ultrasonic transducers which are rotated and/or translated about the object of interest, such as human appendage or extremity. An acoustically dampening chamber containing optoacoustic coupling medium (imaging module) had a volume inside that can be imaged and reconstructed in spherical or cylindrical coordinates. The transducer array and optical fiber bundles were fixed within the imaging module.

Acoustic signals were detected by an arc array of 128 piezo-composite elements having a frequency bandwidth with maximum frequency corresponding to desirable resolution and minimum detectable frequency corresponding to the largest image feature (tissue structure) to be visualized (as an example, an array with bandwidth of 0.1 MHz to 10 MHz can permit accurate quantitative visualization of tissue structures as large as 10 mm with resolution of about 100 micron. The array aperture was spanning an optimal angular aperture of about 150 deg with a radius sufficient to enclose the object of interest. Illumination was set to be in orthogonal optoacoustic mode coming from a bifurcated, randomized fiber bundle with a rectangular output profile. The imaging module was mounted and centered on the rotational stage operated by a computer controlled motor which would rotate around the object under examination (see FIGS. 2A-2C, 4A-4B and 5A-5B for images of a human finger and a live mouse) for multiple complete 360° scans. The remaining components like the digital acquisition hardware, time gain control, and laser were similar to those of the previously described 3D-OAT mouse imaging system that utilized a water tank as an experimental chamber (6, 13).

Figure 2A:
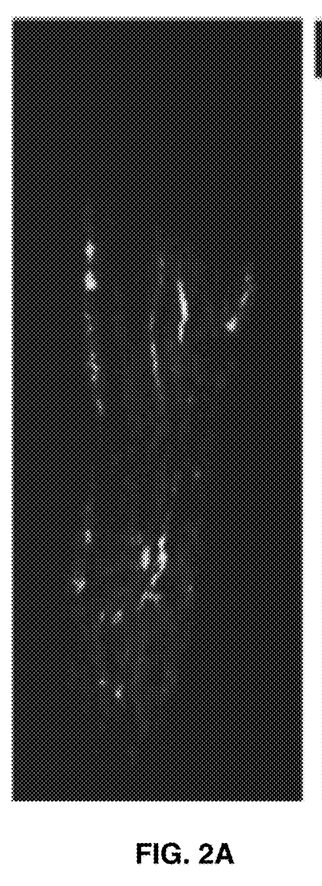
FIGS. 2A-2C show three-dimensional optoacoustic images of a human finger following the hypothermia stress test at 1 minute (FIG. 2A), 3 minutes (FIG. 2B), 7 minutes (FIG. 2C). The colorbar shows the dynamic range of the implemented linear grayscale palette.
Figure 2B:
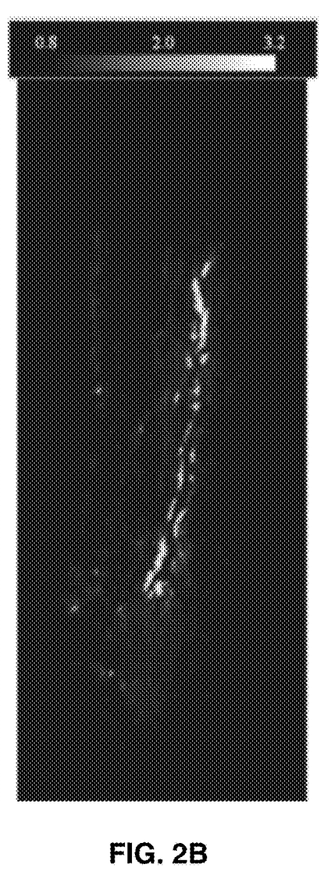
Figure 2C:
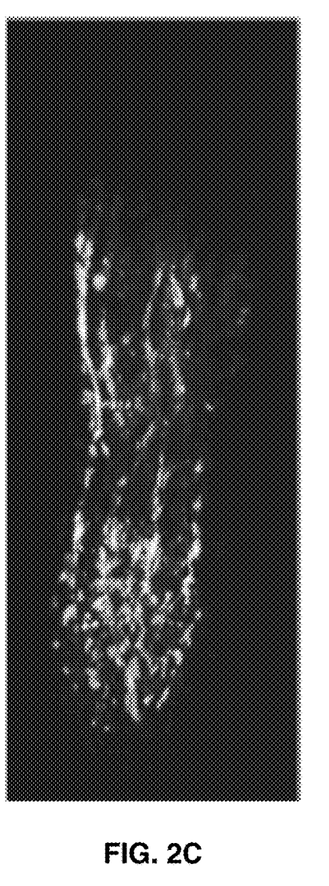

FIGS. 2A-2C illustrates dynamic microangiography of a human finger that was performed using the LOIS-MA system with a rotating imaging module. The hypothermia stress test of a human finger included placing the targeted index finger in the ice-cold water for five minutes. Immediately afterwards, the finger was positioned inside the bowl of LOIS-MA and a series of optoacoustic scans were performed approximately 1, 3, 5, and 7 min after the end of the hypothermia stress test. During the last scan, the volunteer reported return of the normal sensory feelings in the finger under study. Each optoacoustic scan continued for about 30 seconds, providing information about thermoregulatory recovery of the peripheral blood flow averaged over that time frame.

Imaging was performed in vegetable oil, which provided acoustic coupling and also reduced the noise picked up by piezoelements of the acoustic array. Temperature of the coupling oil was recorded before and after the imaging procedure and was all the time between 26° C. and 27° C. A full scan consisted of 150 acquisitions with 2.4° steps made without averaging on every other laser pulse. The total scan time was less than 30 seconds. 1536 samples were recorded per acquisition with a sampling frequency of 20 MHz. The amplifier gain was set to 60 dB. During a scan, the index finger of a volunteer was positioned co-linear and in the proximity to the axis of rotation of the bowl. The motion of the finger was restricted at the most proximal, i.e., metacarpophalangeal, joint using a custom-made hand bracket.

Signal conditioning, image processing, and visualization parameters were frozen with respect to the initial scan in order to observe temporal changes. Signal conditioning involved application of a high-pass filter based on a one-scaled wavelet (18) designed to highlight fine optoacoustic features, like small blood vessels and capillaries. Unfortunately, this type of processing also produced speckled imaging noise commonly found in high frequency reconstructions. It was alleviated using a three dimensional Gaussian filter with a standard deviation of 1.5 voxels. 3D optoacoustic images were reconstructed using filtered radial backprojection (6) and visualized using VolView 2.0 (Kitware, Clifton Park, NY). Using the image intensity histogram, all the values of less than pre-defined threshold were made transparent to get rid of the noise. A linear opacity ramp terminating at the opacity level of 0.05 was followed by a stepwise increase in opacity to the level of 0.3 for the remaining data. Color palette was set to a linear 12-bit grayscale. Gradient opacity mapping was handled by the heuristics of the Strong Edge Detection of VolView with the exception of the zero-opacity point, which was set to the mode of the gradient histogram.

Figure 3A:
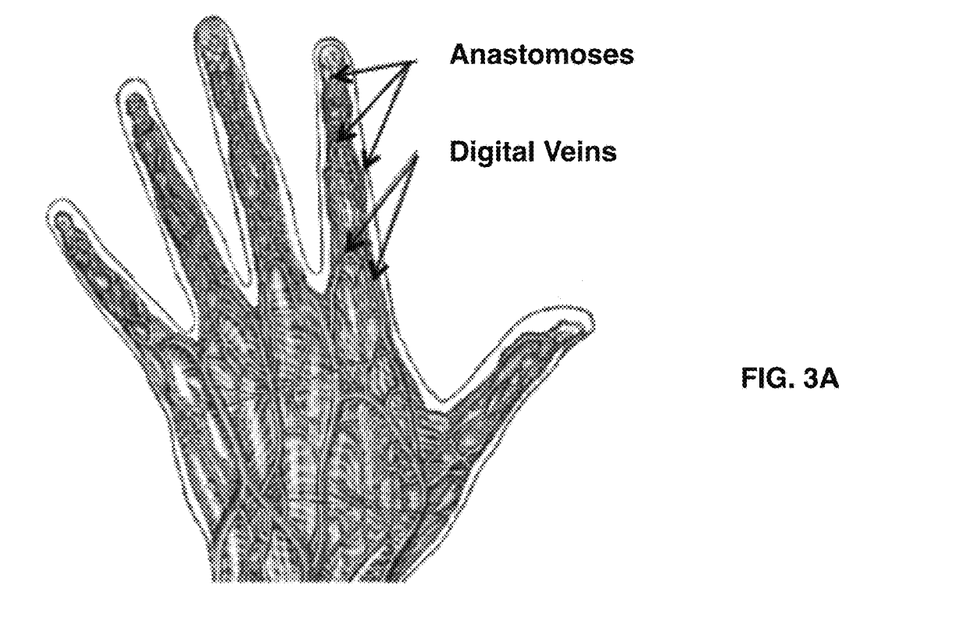
FIGS. 3A-3B depict the radialis indicis (FIG. 3A) and the venal network (FIG. 3B) of the human finger.
Figure 3B:
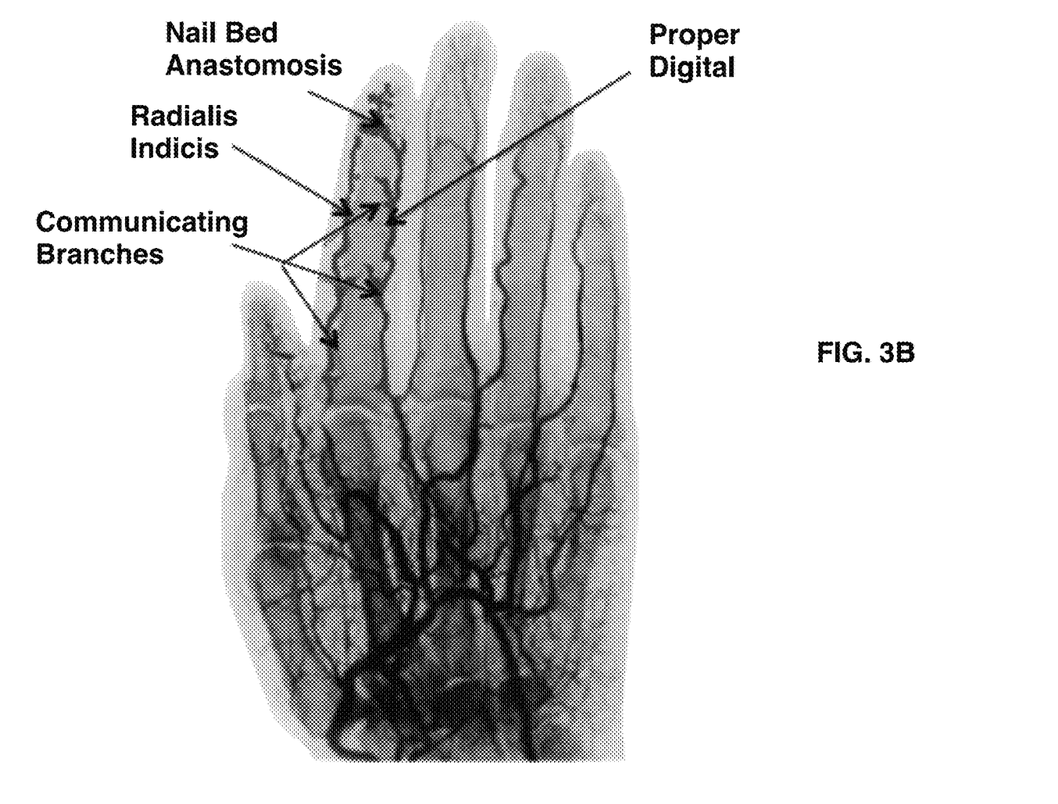

FIGS. 3A-3B depict the vascular anatomy of the human figure. FIG. 3A illustrates the radialis indicis which forms several anastomoses with the proper digital artery. The communicating branches distribute around the joints, supplying structures involved in articulation. The terminal anastomosis found in the nail bed is an important site for regulation of sensory input and thermoregulatory mechanisms. FIG. 3B illustrates the venal network which arises from several anastomoses and converge into proper digital veins that drain via the cephalic vein. Capillary networks, such as the one present in the nail bed are involved in thermoregulation. Vasomotor controls will constrict or increase blood flow through these networks in response to thermal stimuli. The dynamic changes of the local blood flow are dependent on pathological condition of the vasculature.

FIGS. 4A-4B and 5A-5B are images illustrate the results of thermal (hypothermia and hyperthermia) stress tests performed on two mice. Generally, imaging of a mouse was performed in a 1-gallon tank filled with distilled water. Two male Athymic Nude-Foxn1$^{nu}$ mice (Harlan, Indianapolis Indiana) that were 6 to 7 weeks old at the time of the scans were used. They ranged in body mass from 22 to 26 g. Temperature of the water in the tank was continuously monitored with a precision of ±0.1° C. A full scan consisted of ten 360° rotations with 150 acquisitions each, providing a total of 1500 datasets. No averaging was performed during a scan. 1536 samples were recorded per acquisition with a sampling frequency of 20 MHz. The amplifier gain was set to 60 dB. In-vivo mice imaging was done with the use of a mixture of isoflurane and room air that put the mice to sleep and acted as an analgesic. A custom made mouse holder used in our prior studies was used to provide ample imaging area of the body while creating a diving bell for required breathing (21).

Figure 4A:
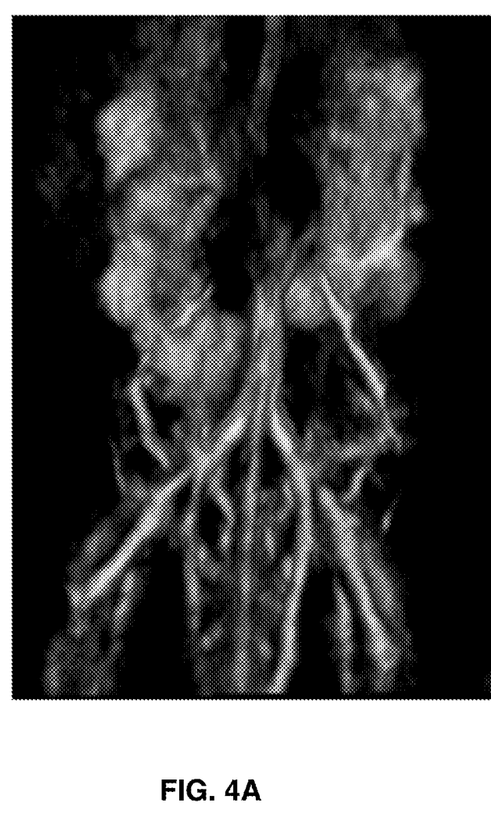
FIGS. 4A-4B show three-dimensional optoacoustic frontal images of a live mouse before and during the hypothermal stress test under normal conditions prior to hypothermia showing kidneys, colon, and vascular network in the lower body (FIG. 4A) and after 20 minutes of hypothermia (FIG. 4B).
Figure 4B:
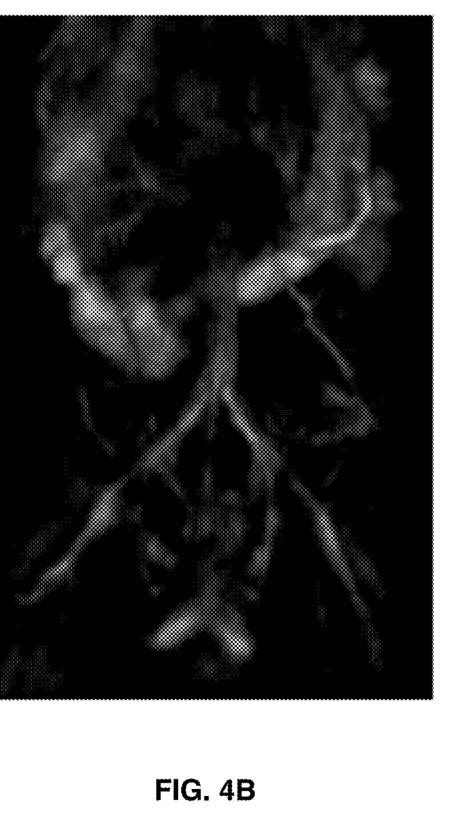

In FIGS. 4A-4B the first mouse was subject to a hypothermia stress test. After an initial OA scanning at normal water temperature of 36° C., the temperature control of a tank was turned off and three out of seven gallons of water in the tank were substituted with distilled water at 4° C. After 60 s of manual stirring, the water in the tank was brought to a steady state room temperature of 25° C. The mouse then was scanned continuously for 7 minutes. After 20 minutes of hypothermia, the image shows significant vasoconstriction with reduced optoacoustic intensity and now clearly identified colon.

Figure 5A:
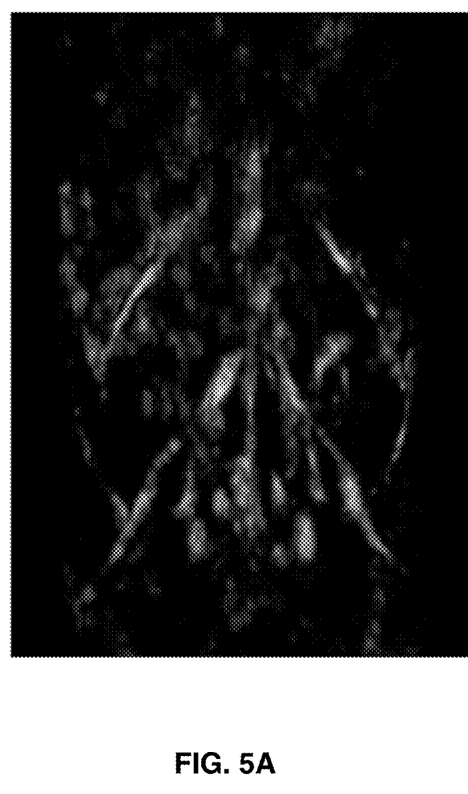
FIGS. 5A-5B show three-dimensional optoacoustic frontal images of a live mouse before and during the hyperthermal stress test under normal conditions prior to hypothermia showing the vascular network in the lower body (FIG. 5A) and after 15 minutes of hyperthermia (FIG. 5B).
Figure 5B:
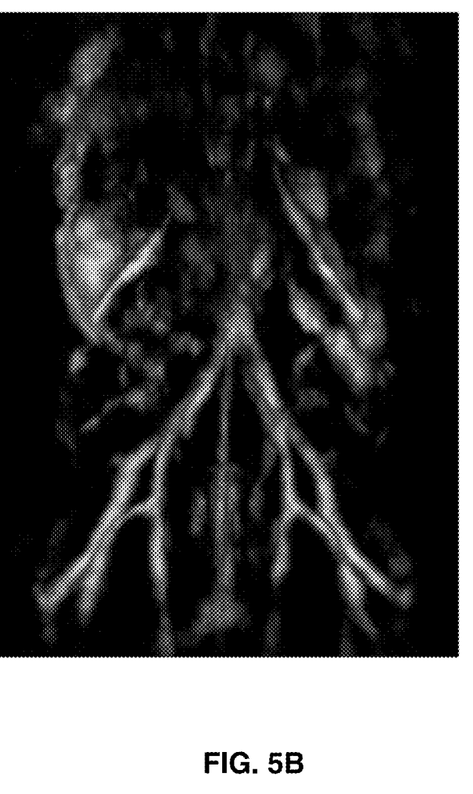

In FIGS. 5A-5B the second mouse was subject to a hyperthermia stress test. In that after an initial OA scanning at normal water temperature of 36° C., the temperature control of a tank was turned to a maximum level of 45° C. and two out of seven gallons of water in the tank were substituted with boiling water. After 60 s of manual stirring, the water in the tank was brought to a quasi-steady state at 45° C. The mouse then was scanned continuously for 7 minutes. Dynamic optoacoustic angiography of a mouse under those thermal stress tests provided information about systemic thermoregulatory response to a moderate short-term hypo- and hyperthermia. After 15 minutes of hyperthermia, the image shows significant vasodilation with increased optoacoustic intensity and now clearly identified portion of the liver.

Figure 6A:
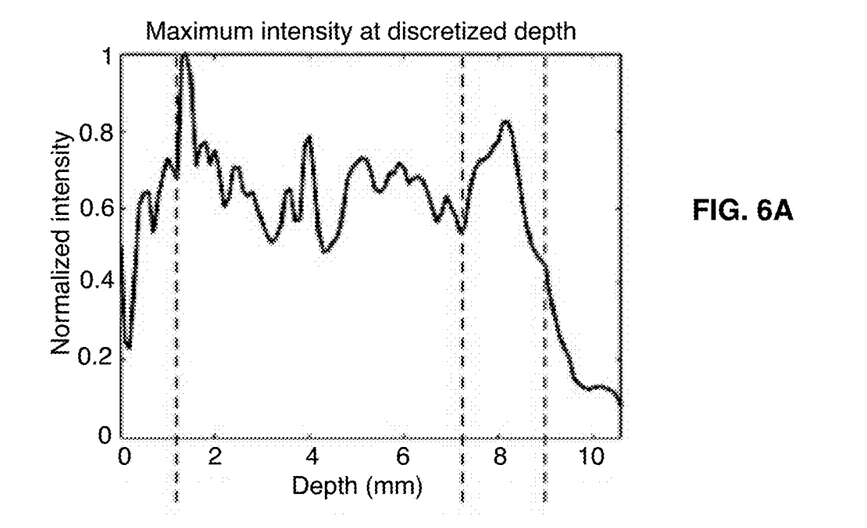
FIGS. 6A-6B present the experimental curves of the optoacoustic image brightness as a function of depth measured from mouse skin on 3D optoacoustic images acquired at 1064 nm (FIG. 6A) and 757 nm (FIG. 6B). These curves show the presence of background absorbed optical energy and deviation from the background due to the presence of larger blood vessels. These curves enable normalization of the optical fluence through the depth of the volume of interest.
Figure 6B:
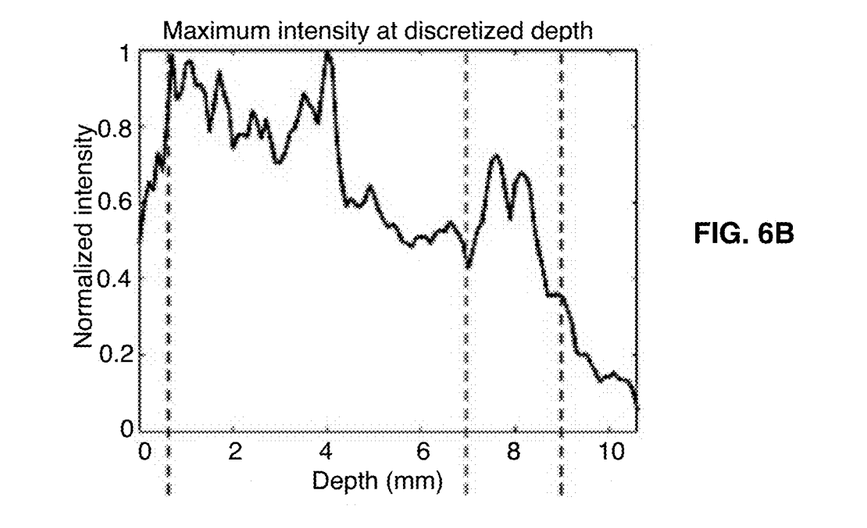

FIGS. 6A-6B present the experimentally measured curves of the absorbed optical energy as a function of depth starting from the skin of a mouse. These curves show the presence of background optical absorption by unresolved microvasculature (background optoacoustic image brightness) and deviation from the background due to the presence of larger blood vessels. This type of measurement was only possible from the optoacoustic image acquired with ultrawide band ultrasonic transducers sensitive in the lower ultrasonic frequency range, a feature not available in any other optoacoustic imaging systems. The curves measured at 1064 nm (A) and 757 nm (B) were used to estimate the effective optical attenuation through the depth of the volume of interest according to Beer-Lambert law. These curves demonstrate the new method to normalize the optical fluence through the depth of the volume of interest displayed on an optoacoustic image brightness by compensating for the effective optical attenuation at each wavelength used in the cycle of 2 cycling laser wavelengths (1064 nm and 757 nm).

Figure 7A:
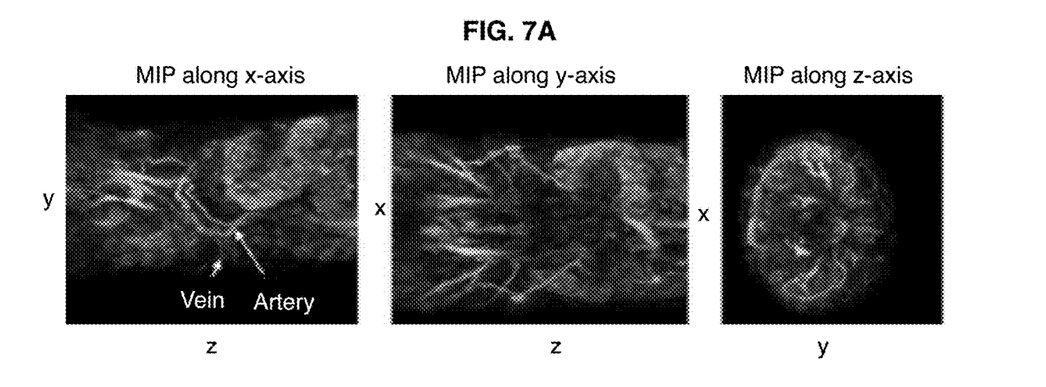
FIGS. 7A-7B show maximum intensity projection (MIP) optoacoustic images of a live mouse body acquired at 1064 nm (FIG. 7A) and 757 nm (FIG. 7B). The 3 images of three orthogonal views were processed through normalization by equalizing the optical fluence through the depth of tissue by compensating for the effective optical attenuation.
Figure 7B:
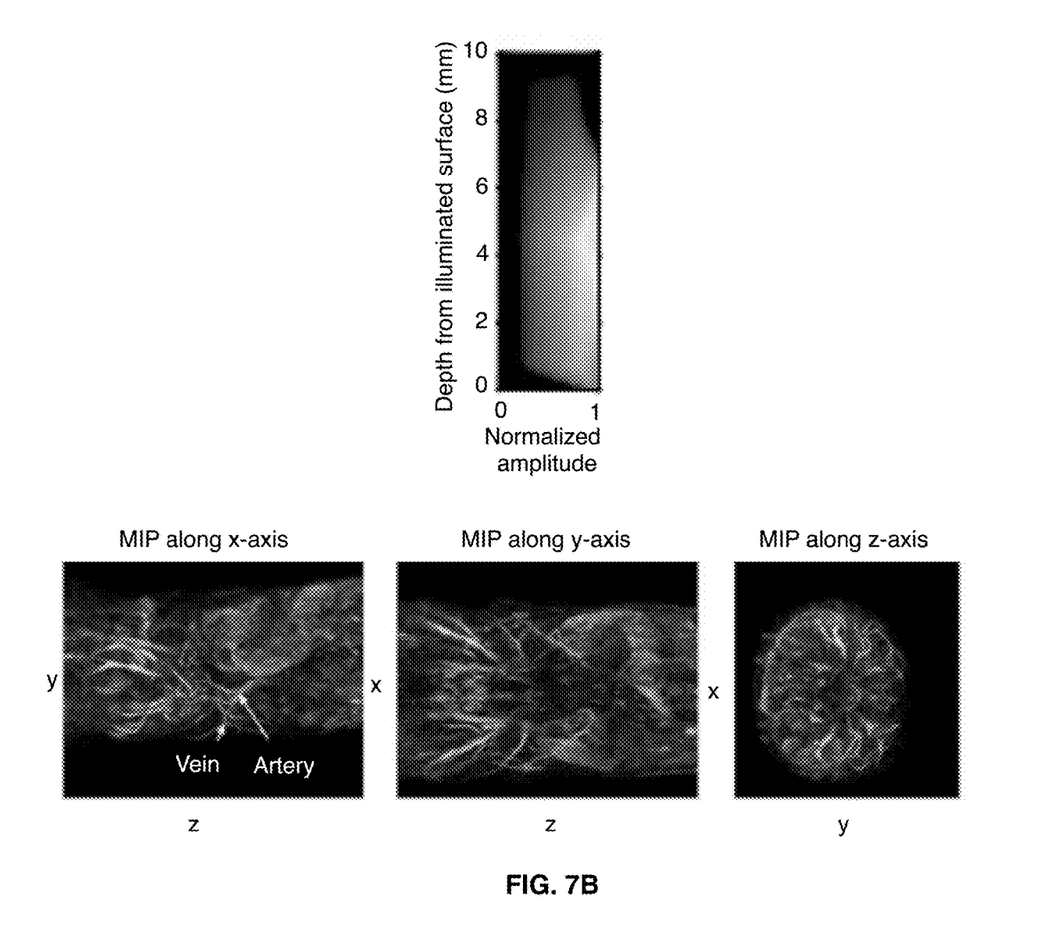

FIGS. 7A-7B shows maximum intensity projection optoacoustic images of a live mouse body acquired at 1064 nm (A) and 757 nm (B) and presented along three orthogonal axes: x,y,z. The two sets of 3 images were processed through normalization of the incident optical fluence on the surface of the mouse and further processed by normalizing the optical fluence through the depth of tissue by compensating for the effective optical attenuation. As a result of the optical fluence normalization the entire vasculature and organs of this mouse became visible through the entire body and their brightness became quantitatively proportional to the optical absorption coefficient.

In summary, provided herein is a quantitative optoacoustic tomography (qOAT) system designed for dynamic angiography of vasculature and microvasculature in vivo. The clinically viable performance and utility of this system is enabled by a number of novel features and inventive steps, including: (1) utilization of a pulsed laser capable of rapid cycling of 2 or more wavelengths preferentially absorbed by hemoglobin and oxyhemoglobin, which permits coregistration of images at different wavelengths enabling mathematical operations with the images; (2) ultrawide-band ultrasonic transducers sensitive not only in the high frequency range (about 15 MHz) providing excellent resolution, but also in the low frequency range (about 50 kHz and below) providing high volumetric contrast and enabling quantitative measurements of the background absorbed optical energy from 3D optoacoustic images; (3) a method for normalization of the optical fluence on the surface and through the depth of the volume of interest enabling clear visualization of vasculature through the entire depth of tissue and quantitative measurements of the functional parameters of the total hemoglobin and blood oxygen saturation.

The following references are cited herein.
1. Hu S. and Wang L. V. J. Biomed. Opt. 2010, 15(1), 011101. doi: 10.1117/1.3281673.
2. Disa et al. Plastic and reconstructive surgery 99(1), 136-144 (1997).
3. Toprak et al. Clinical rheumatology 28(6), 679-683 (2009).
4. Wang et al. Rheumatology 47(8), 1239-1243 (2008).
5. Favazza et al. Proceedings SPIE, Vol. 7564, 75640Z (2010).
6. Rosato et al. Rheumatology 50(9), 1654-1658 (2011).
7. Nadler et al. Pain Physician. 2004, 7: 395-399.
8. Brecht, et al. Journal of biomedical optics 14(6), 064007 (2009).
9. Fronheiser et al. Journal of biomedical optics 15(2), 021305 (2010).
10. Tsytsarev et al. Journal of biomedical optics 16(7), 076002 (2011).
11. Beard P. Interface Focus 1, 602-631 (2011).
12. Oraevsky, A. A. and Karabutov, A. A., "Optoacoustic Tomography", CRC Press, Boca Raton, 34/31-34/34 (2003).
13. Ermilov et al. Proceedings SPIE vol. 7564, 75641W (2010).
14. Mobley J. and Vo-Dinh T. "Optical properties of tissue", CRC Press, Boca Raton, 2/1-2/75 (2003).
15. Cox et al. Quantitative spectroscopic photoacoustic imaging: a review. J. of Biomedical Optics, 17(6), 061202 (2012).
16. Su et al. Proceedings SPIE 7899, 78994B (2011).
17. Wang et al. Proceedings SPIE 6856, 685604 (2008).
18. Sun Y. and Jiang, H. Proceedings SPIE 7258, 72584G (2009).
19. Pozos R. S. and Danzl, D. F., "Human physiological responses to cold stress and hypothermia", TMM Publications, Washington, D.C., 351-382 (2002).
20. Ermilov S., et al. Proceedings SPIE 6856, 685603 (2008).
21. Su, et al. Proc. of SPIE 8089, 808902 (2011).
22. Oraevsky, et al., U.S. Pat. No. 5,840,023
23. Wang et al. U.S. Publication No. US2008/0173093 A1.
24. Sudo et al. U.S. Publication No. 2012/0285248 A1.

What is claimed is:

1. A quantitative optoacoustic tomography system for dynamic angiography of functional parameters in a subject comprising:
   a pulsed laser operating in a wavelength cycling mode with at least two wavelengths in the cycle; wherein one of the wavelengths is absorbed by hemoglobin and another of the wavelengths is absorbed by oxyhemoglobin;
   a fiberoptic bundle light delivery system with randomized fibers to provide a homogeneous illumination beam for delivery of optical energy to an entire volume of interest in the subject;
   an imaging module filled with an optoacoustic coupling medium at a precisely controlled temperature, said temperature varied in a range of at least 12° C. to 45° C. tolerable by the subject;
   an array of ultrawide-band ultrasonic transducers with an equal sensitivity over a range of ultrasonic frequencies of at least 50 KHz to 15 MHz for detection of optoacoustic signals with high resolution and without distortions of quantitative volumetric contrast;
   a circulation system in fluid communication with the optoacoustic coupling medium comprising a thermostat and configured to cool and heat the optoacoustic coupling medium and to maintain the optoacoustic coupling medium at a constant temperature;
   a multichannel electronic data acquisition system with ultrawide-band analog amplifiers, analog-to-digital converters, a memory, and a field programmable gate array microprocessor for signal processing, storage and transmission;
   a computer with a multicore CPU and a multicore GPU and software configured for system control, for regulation of the thermostat and for reconstruction and processing of three-dimensional quantitative tomography images of the functional diagnostic parameters measured at different physiological temperatures for dynamic angiography of the volume of interest; said software enabling processor-executable instructions configured to at least:
   a) stabilize the optoacoustic coupling medium at a normal physiological temperature for the subject;
   b) perform an optoacoustic imaging scan of an appendage positioned into the imaging module at the normal physiological temperature with the at least two cycling laser wavelengths;
   c) change the temperature of the optoacoustic coupling medium in steps from the normal physiological temperature to a maximum safe temperature of about 42° C. or to a minimum safe temperature of about 15° C.;
   d) perform an optoacoustic imaging scan at each step from the normal physiological temperature and at each temperature changed in a range from the maximum safe temperature of the optoacoustic coupling medium to the minimum safe temperature of the optoacoustic coupling medium and to precisely stabilize each temperature during each optoacoustic imaging scan;

e) save, analyze and process the optoacoustic signals acquired at each step of changing the temperature;

f) reconstruct two or more spatially coregistered three-dimensional optoacoustic images that correspond to the at least two cycling laser wavelengths at each step of changing the temperature of the optoacoustic coupling medium;

g) perform an optical fluence normalization or equalization on a surface of the appendage and through a depth of the entire volume of interest for each laser wavelength used for imaging to make accurate quantitative images from the spatially coregistered three-dimensional optoacoustic images h) perform mathematical operations on the quantitative images; and i) display the quantitative images of functional and anatomical parameters in the volume of interest; and a high-resolution display in electronic communication with the computer and configured for presentation of three-dimensional angiographic images of the volume of interest, 2D slices through the volume of interest or quantitative values of the functional parameters of vasculature and microvasculature or a combination thereof.

2. The optoacoustic imaging system of claim 1, wherein the array of ultrawide-band ultrasonic transducers is scannable about the volume of interest in a rotational mode or a translational mode or a combination thereof.

3. The optoacoustic imaging system of claim 1, wherein said functional diagnostic parameters are total hemoglobin and blood oxygen saturation.

4. The optoacoustic imaging system of claim 1, wherein said functional diagnostic parameters are concentrations of exogenously administered diagnostic, therapeutic or contrast agents.

5. The optoacoustic imaging system of claim 1, wherein the volume of interest is an appendage of the subject; wherein the appendage is an arm, a hand, fingers, a leg, a foot, or toes.

6. The optoacoustic imaging system of claim 1, said system configured to evaluate blood flow, ischemia, hyperemia, or to assist in an administration of hemodialysis.

7. The optoacoustic imaging system of claim 1, wherein the at least two cycling wavelengths comprise the visible spectrum and the near-infrared spectrum.

8. The optoacoustic imaging system of claim 7, wherein the at least two cycling wavelengths are 757±5 nm and 845±5 nm.

9. The optoacoustic imaging system of claim 7, wherein the at least two cycling wavelengths comprise at least the isosbestic point wavelength of 800±5 nm of equal absorption by hemoglobin and oxyhemoglobin.

10. The optoacoustic imaging system of claim 1, further comprising an ultrasound imaging system configured for coregistration of functional images and anatomical images of the volume of interest.

11. The optoacoustic imaging system of claim 10, wherein the ultrasound imaging system is configured to generate ultrasound electrically or via laser.

12. A method for quantitative optoacoustic tomography to assess conditions of vasculature and microvasculature in a subject using dynamic angiography of an appendage, comprising the steps of a) stabilizing an optoacoustic coupling medium contained within an imaging module at a normal physiological temperature for the subject;

b) positioning the appendage into the imaging module;

c) performing an optoacoustic imaging scan of the appendage at the normal physiological temperature with at least two cycling laser wavelengths;

d) changing the temperature of the optoacoustic coupling medium in steps from the normal physiological temperature to a maximum safe temperature of about 42° C. or to a minimum safe temperature of about 15° C. safely tolerable by the subject;

e) performing an optoacoustic imaging scan at each step of changing the physiological temperature and then at a stabilized temperature in a range from the maximum safe temperature to the minimum safe temperature of the optoacoustic coupling medium;

f) saving, analyzing and processing optoacoustic signals acquired at each step of changing the temperature;

g) reconstructing two or more spatially coregistered three-dimensional optoacoustic images corresponding to the at least two cycling laser wavelengths at each step of changing the temperature of the optoacoustic coupling medium;

h) performing an optical fluence normalization or equalization on the surface of the appendage and through a depth of the entire volume of interest for each laser wavelength used for imaging thereby making accurate quantitative images from the spatially coregistered three-dimensional optoacoustic images;

i) performing mathematical operations on the quantitative images; and j) displaying the quantitative images of functional and anatomical parameters in the volume of interest.

13. The method of claim 12, wherein the quantitative images of functional and anatomical parameters displayed in step j) are differential functional images of functional diagnostic parameters as they change over time and as a function of temperature; said method further comprising:

k) diagnosing a medical condition of the subject or a state of vascular and microvascular systems of the subject based on the differential functional images of functional diagnostic parameters.

14. The method of claim 12, wherein functional and anatomical details of a peripheral vasculature characterize a thermoregulatory response and other mechanisms responsible for vasomotor activity.

15. The method of claim 12, wherein the appendage is an arm, a hand, fingers, a leg, a foot, or toes.

* * * * *